United States Patent
Schoenberg (10) Patent No.: US 8,155,977 B2
(45) Date of Patent: Apr. 10, 2012

(54) RULE MANAGEMENT METHOD AND SYSTEM

(75) Inventor: Roy Schoenberg, Boston, MA (US)

(73) Assignee: The TriZetto Group, Inc., Greenwood Village, CO (US)

(*) Notice: Subject to any disclaimer, the term of this patent is extended or adjusted under 35 U.S.C. 154(b) by 3031 days.

(21) Appl. No.: 10/825,352

(22) Filed: Apr. 15, 2004

(65) Prior Publication Data

US 2005/0234739 A1    Oct. 20, 2005

(51) Int. Cl.
*G06Q 10/00* (2012.01)

(52) U.S. Cl. .................................. 705/2; 705/3
(58) Field of Classification Search .......... 705/2–4; 600/300–301
See application file for complete search history.

(56) References Cited

U.S. PATENT DOCUMENTS

| | | | |
|---|---|---|---|
| 5,937,037 A | 8/1999 | Kamel et al. | |
| 6,041,347 A * | 3/2000 | Harsham et al. | 709/220 |
| 6,211,783 B1 | 4/2001 | Wang | |
| 6,398,727 B1 * | 6/2002 | Bui et al. | 600/300 |
| 6,463,417 B1 | 10/2002 | Schoenberg | |
| 6,656,115 B1 | 12/2003 | Miyazaki et al. | |
| 6,754,635 B1 | 6/2004 | Hamlin et al. | |
| 7,304,582 B2 * | 12/2007 | Kerr et al. | 340/573.4 |
| 7,447,663 B1 * | 11/2008 | Barker et al. | 705/78 |
| 2002/0016719 A1 | 2/2002 | Nemeth et al. | |
| 2002/0077856 A1 * | 6/2002 | Pawlikowski et al. | 705/2 |
| 2004/0205540 A1 * | 10/2004 | Vulpe et al. | 715/511 |
| 2005/0125252 A1 * | 6/2005 | Schoenberg | 705/2 |
| 2005/0216313 A1 * | 9/2005 | Claud et al. | 705/3 |

OTHER PUBLICATIONS

International Search Report & Written Opinion issued for PCT/US2005/012587 dated Nov. 30, 2006.

* cited by examiner

*Primary Examiner* — Vivek Koppikar
(74) *Attorney, Agent, or Firm* — Dawn-Marie Bey; King & Spalding LLP (57) ABSTRACT

A rule processing method includes defining a target group of patients chosen from a group of existing patients. An action to be taken concerning one or more patients within the target group of patients is defined, and an execution time for the action is scheduled.

6 Claims, 8 Drawing Sheets

RULE MANAGEMENT METHOD AND SYSTEM

RELATED APPLICATIONS

The following U.S. patent is hereby incorporated by reference into the subject application as if set forth herein in full: (1) U.S. Pat. No. 6,463,417, entitled "Method of Distributing Health Information".

FIELD OF THE INVENTION

This invention relates to rule management and, more particularly, to rule management within a medical records management system

BACKGROUND

Traditionally, the medical records of a patient are paper-based medical records, in which each medical service provider (that provides medical services to the patient) maintains a separate medical record for that patient.

Often, patients who are within certain age brackets or have certain conditions are uninformed of information that may be beneficial to their particular situation. Examples of these situations include the timing of prostate exams for men and mammograms for women.

Unfortunately, with paper-based medical records, the medical service provider would need to manually review the medical records of each of their patients to determine which groups of patients should receive medical information, come in for certain tests, or learn about certain diseases and warning signs, for example.

Currently, paper-based medical records are slowly being converted into electronic, centrally-located databases that are accessible by various medical service providers.

SUMMARY OF THE INVENTION

In one implementation, a rule processing method includes defining a target group of patients chosen from a group of existing patients. An action to be taken concerning one or more patients within the target group of patients is defined, and an execution time for the action is scheduled.

One or more of the following features may also be included. Defining a target group of patients may include processing the medical records of the existing patients to determine which of the medical records define the existence of a selected condition, such as a medical condition, physical criteria, habit, or activity of a patient.

Defining an action may include one or more of: posting a HTML link for a patient; posting a message for a patient; providing a tool to a patient; transmitting an email to a patient; updating a patient's medical record; transmitting a pop-up message to a patient; recommending that a patient join a discussion board; providing a patient with medical information; providing a medical report to a patient; providing a medical report to a third party; executing a program; and notifying a third party.

Scheduling the execution time may include specifying: a single, non-recurring, execution time; a plurality of non-recurring execution times; or a recurring execution time.

The action concerning the one or more patients within the target group of patients may be executed on or after the execution time.

In another implementation, a rule processing method includes: determining, for a specific rule, a target group of patients. The action to be taken, for the specific rule, is determined concerning one or more patients within the target group of patients. Further, an execution time for the action is determined for the specific rule. The action concerning the one or more patients within the target group of patients is executed on or after the execution time.

In another implementation, a rule processing computer-based method includes processing a multi-portion medical record for each of a group of existing patients to define a target group of patients chosen from the group of existing patients. Each portion of the medical record is assigned a confidentiality level. An action to be taken is defined concerning one or more patients within the target group of patients. An execution time for the action is scheduled.

The above-described methods may also be implemented as a sequence of instructions executed by a processor.

The details of one or more implementations is set forth in the accompanying drawings and the description below. Other features and advantages will become apparent from the description, the drawings, and the claims.

DETAILED DESCRIPTION OF THE PREFERRED EMBODIMENTS

Figure 1:
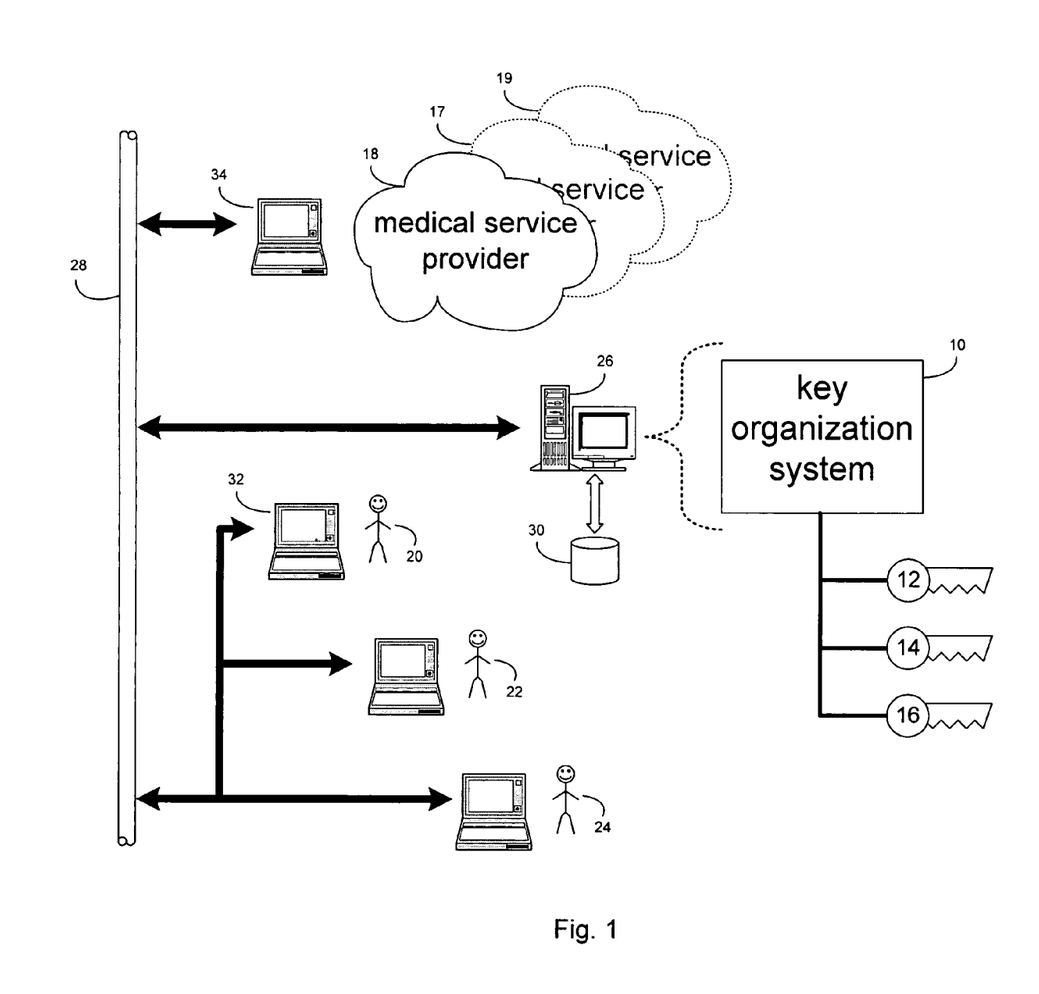
FIG. 1 is a diagrammatic view of key organization system coupled to a distributed computing network.

Referring to FIG. 1, there is shown a key organization system 10 that manages the various access keys 12, 14, 16 possessed by a medical service provider 18. Access keys 12, 14, 16 are provided to medical service provider 18 by various patients 20, 22, 24.

Key organization system 10 typically resides on and is executed by a computer 26 that is connected to network 28. Computer 26 may be a web server running a network operating system, such as Microsoft Window 2000 Server™, Novell Netware™, or Redhat Linux™. Typically, computer 26 also executes a web server application, such as Microsoft IIS™, Novell Webserver™, or Apache Webserver™, that allows for HTTP (i.e., HyperText Transfer Protocol) access to computer 26 via network 28.

The instruction sets and subroutines of key organization system 10, which are typically stored on a storage device 30 coupled to computer 26, are executed by one or more processors (not shown) and one or more memory architectures (not shown) incorporated into computer 26. Storage device 30 may be, for example, a hard disk drive, a tape drive, an optical drive, a RAID array, a random access memory (RAM), or a read-only memory (ROM).

As will be explained below in greater detail, a patient (e.g., patient 20) typically provides an access key (e.g., key 12) to medical service provider 18 through a patient computer 32, which is also connected to network 28. Additionally, medical service provider 18 accesses key organization system 10 through a client computer 34.

Figure 2:
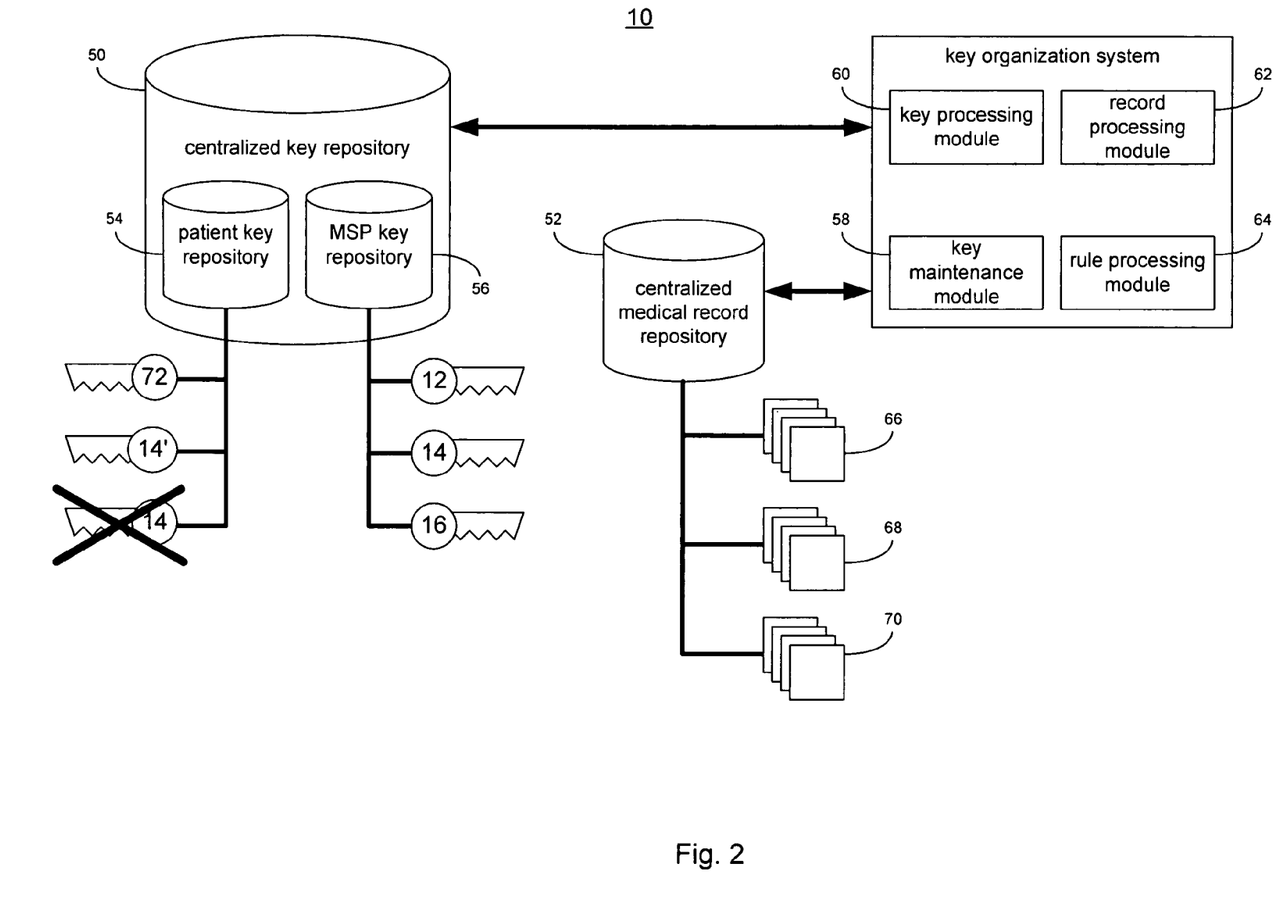
FIG. 2 is a more-detailed diagrammatic view of the key organization system of FIG. 1.

Referring also to FIG. 2, key organization system 10 includes a centralized key repository 50 and a centralized medical records repository 52. Typically, centralized key repository 50 includes one or more patient key repositories 54 and one or more MSP (i.e., medical service provider) key repositories 56. Additionally, key organization system 10 includes a key maintenance module 58, a key processing module 60, a record processing module 62, and a rule processing module 64, each of which will be discussed below in greater detail.

Centralized medical records repository 52 allows for the centralized storage of medical records 66, 68, 70 that concern various patients 20, 22, 24 respectively. As disclosed in U.S. Pat. No. 6,463,417, medical records 66, 68, 70 are typically divided into portions or levels, in that certain portions are considered more confidential than other portions. For example, a portion/level of the medical record that may be considered the least confidential might include general patient identification information and information concerning the patient's blood type and allergies. A portion/level of a medical record that may be considered to have an intermediate level of confidentiality might include information concerning the serological data, psychiatric data, cardiology data, and genetic data. A portion/level of the medical record that may be considered highly confidential may include infectious disease (e.g., HIV, and sexually transmitted diseases) data.

This specific assignment of confidentiality levels and the apportionment of the medical record into various portions/levels is for illustrative purposes only and is not intended to limit the scope of this disclosure.

Medical records 66, 68, 70 may be incrementally generated/configured online by the various medical service providers that provide care to patients 20, 22, 24. Alternatively, existing medical records may be uploaded (i.e., transferred) to medical records repository 52 from a remote storage location (not shown).

Figure 3:
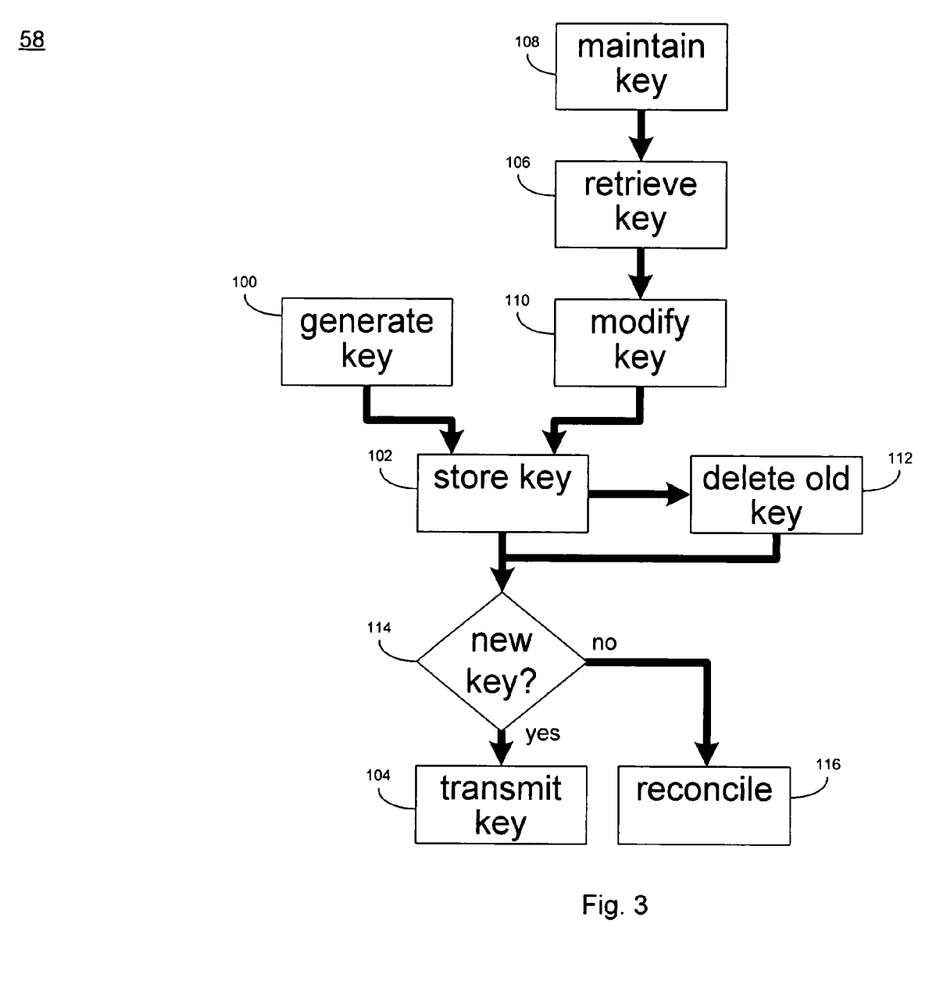
FIG. 3 is a block diagram of a key maintenance module of the key organization system of FIG. 1.

Referring also to FIG. 3, patients 20, 22, 24 use key maintenance module 58 to generate 100 access keys 12, 14, 16 that grant access to various portions of their respective medical records 66, 68, 70. Accordingly, though the use of key maintenance module 58, the patient can generate access keys that not only regulate who has access to their medical records, but can also regulate the level of access (i.e., which portions of a patient's medical record are viewable by the medical service provider to which the key is provided). Examples of access keys 12, 14, 16 are passwords (that allow access to various portions of a medical record) and decryption keys (that decrypt various portions of an encrypted medical record).

Typically, key maintenance module 58 is a web-enabled application that is accessed by the patients (e.g., patient 20) through a browser application (e.g., Microsoft Internet Explorer™, or Netscape Navigator™) that is running on patient computer 32. Alternatively, key maintenance module 58 may be a local application that is executed locally on patient computer 32.

As stated above, key maintenance module 58 allows a patient to generate 100 an access key for a specific medical service provider that grants, to that medical service provider, a defined level of access to that patient's medical records. Once this access key is generated, it is stored 102 on the patient key repository 54 assigned to that patient (i.e., the patient generating the access key).

Once stored 102, the access key is transmitted 104 to the appropriate medical service provider (e.g., medical service provider 18). This transmission of the access key may be implemented by transferring the access key from the patient to the medical service provider. This may occur by attaching the access key to an email that is transmitted to the medical service provider. Once received, the medical service provider may then transfer the newly-generated key to the key processing module 60 (to be discussed below in greater detail) of the key organization system 10. Alternatively, the patient may directly transfer the newly-generated key to the key processing module 60 of the key organization system 10.

Figure 4:
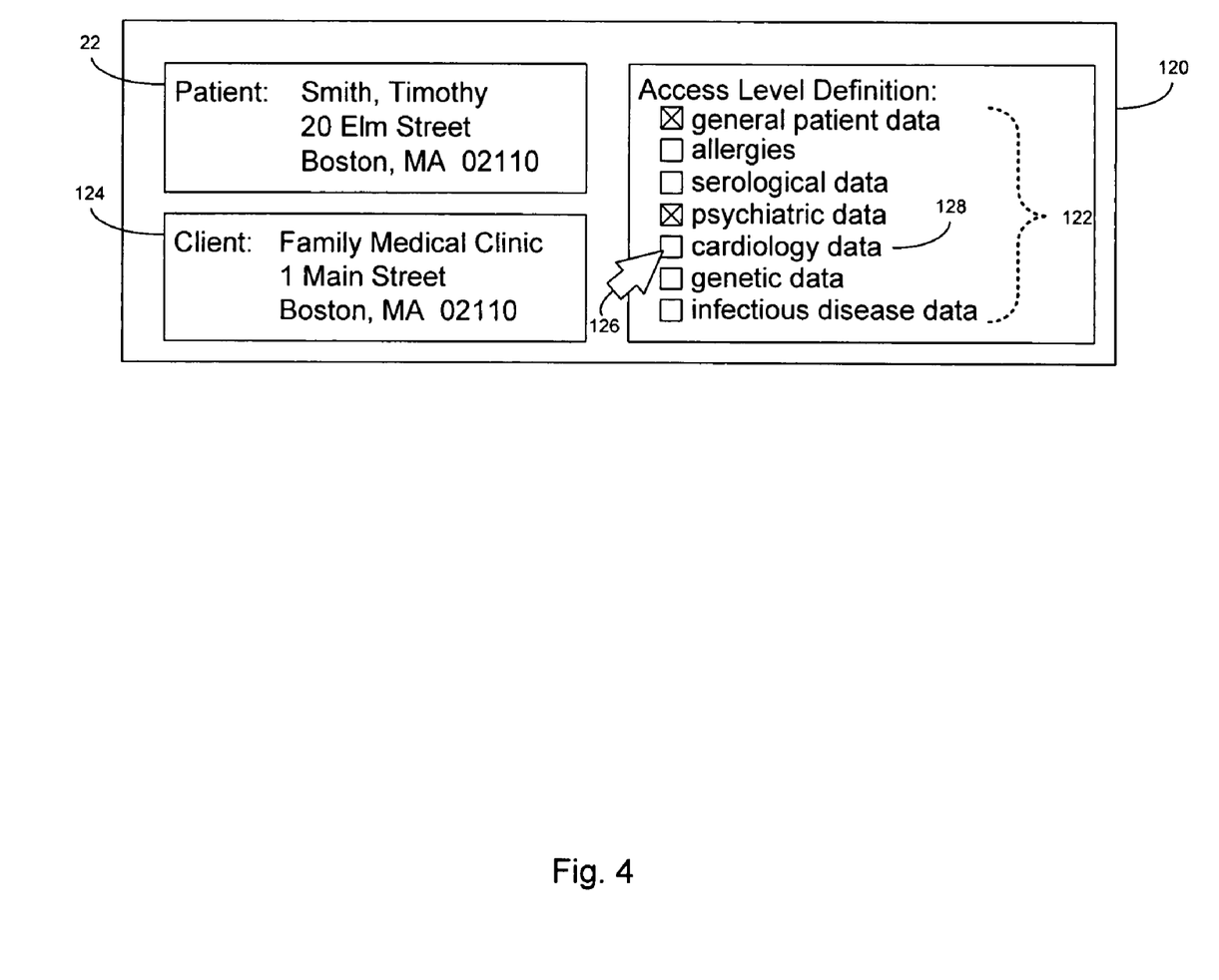
FIG. 4 is a diagrammatic view of a key configuration display screen rendered by the key organization system of FIG. 1.

Referring also to FIG. 4, when a patient is generating an access key (e.g., access key 14) for a medical service provider, key maintenance module 58 provides the patient (e.g., patient 22) with a rendered screen display 120 that allows the patient to select one or more access parameters 122 that define the access level granted to that particular medical service provider. Display 120 identifies the patient (i.e., Timothy Smith; patient 22) and allows the patient to select the recipient 124 of the access key being generated by the patient. In this example, the recipient 124 is Family Medical Clinic; medical service provider 18.

As stated above, medical records 66, 68, 70 are typically divided into portions or levels, such that certain portions are considered more confidential than other portions. The access parameters 122 selected (i.e., checked) by the patient define the various portions of the patient's medical record that the medical service provider is going to have access to. In this particular case, the access key being generated by patient Timothy Smith (i.e., patient 22) for the Family Medical Clinic (i.e., medical service provider 18) is going to allow the medical service provider to access only two portions of the patient's medical record, namely the general portion and the psychiatric data. As the remaining access parameters are unchecked, medical service provider 18 is going to be prohibited from accessing any other portion of the patient's medical record. When generating the access key, the patient selects the appropriate access parameters 122 using a mouse pointer 126 (or some other pointing device, not shown).

Figure 5:
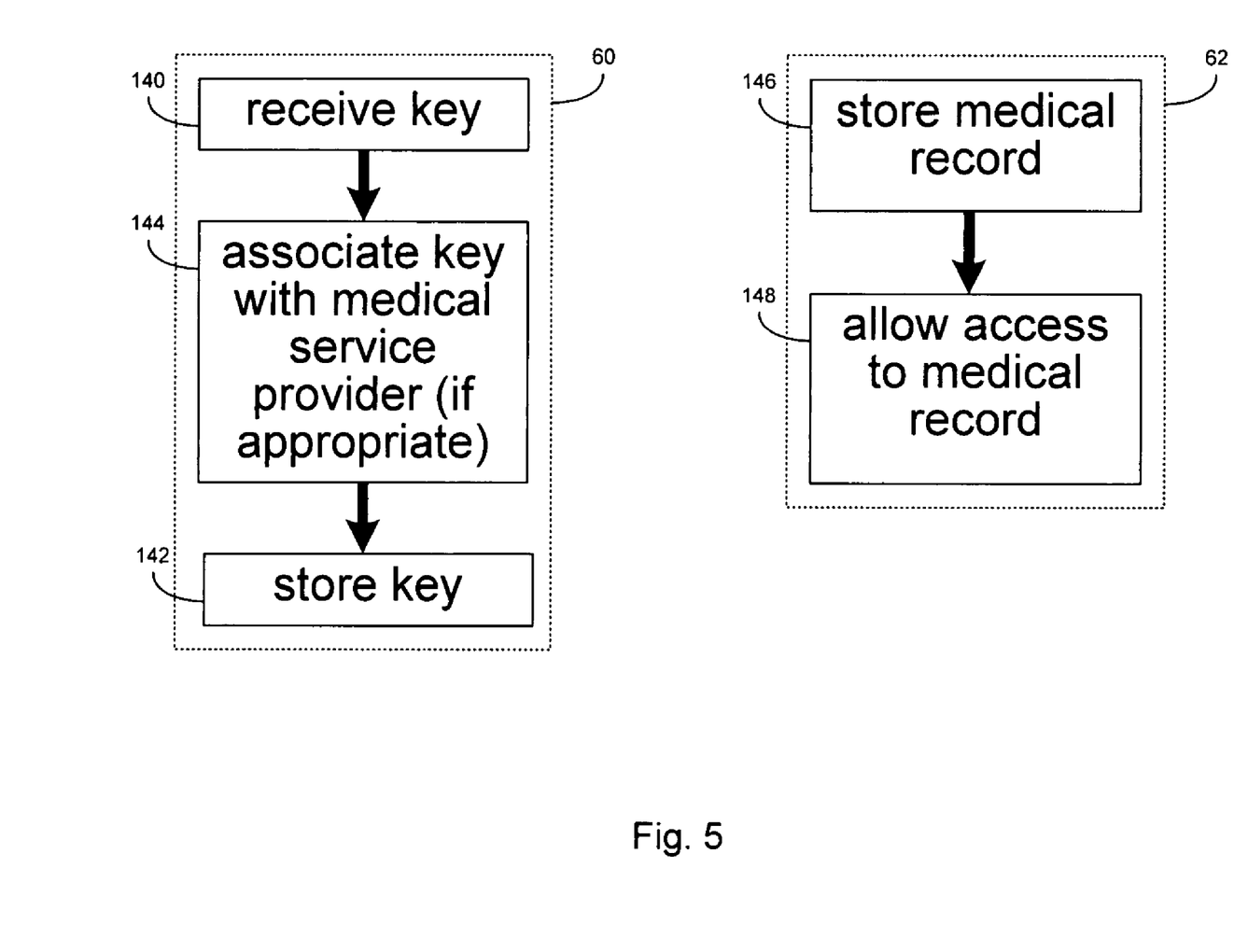
FIG. 5 is a block diagram of a key processing module and a record processing module of the key organization system of FIG. 1.

Now referring to FIGS. 1, 2 and 5, regardless of the manner in which the patient transfers the access key to the medical service provider, the access key will ultimately be received 140 by key processing module 60, which receives any access keys (e.g., keys 12, 14, 16) generated and transmitted by patients 20, 22, 24. Once these keys are received 140, they are stored 142 on the MSP key repository 56 within the centralized key repository 50. Additionally, if key organization system 10 is servicing multiple medical service providers (e.g., medical service providers 17 and 19 in addition to medical service provider 18), the received keys are associated 144 with the appropriate medical service provider, thus preventing the keys transmitted to a first provider from being available to a second provider and allowing storage in the appropriate MSP key repository.

When medical records are initially received, initially generated, and/or edited, record processing module 62 stores 146 the medical record on centralized medical record repository 52. Typically, medical record repository 52 is a database that allows for the organized storage and retrieval of the medical records 66, 68, 70.

Once these medical records are stored on medical record repository 52, record processing module 62 allows the medical service provider 18 to access 148 the medical records 66, 68, 70 stored on medical records repository 52. However, the medical service provider 18 is only given access to the portions of the medical records for which the medical service provider 18 possesses the appropriate key. For example, assume that medical service provider 18 is a medical clinic that provides an array of medical services to its patients. Further, assume that patient 20 uses medical service provider 18 for all of their medical needs; patient 22 uses medical service provider 18 solely for treatment of depression; and patient 24 uses medical service provider 18 solely for treatment of HIV.

Concerning the access keys generated by each of these patients for medical service provider 18: patient 20 would typically provide medical service provider 18 with an access key (i.e., key 12) that grants access to their entire medical record; patient 22 would typically provide medical service provider 18 with an access key (i.e., key 14) that grants access to the general and psychiatric portions of their medical record; and patient 22 would typically provide medical service provider 18 with an access key (i.e., key 16) that grants access to the general and infectious disease portions of their medical record.

Record processing module 62 is typically a web-enabled application that is accessed by the medical service provider 18 through a browser application (e.g., Microsoft Internet Explorer™, or Netscape Navigator™) that is running on client computer 34. Typically, medical service provider 18 logs into key organization system 10 using an encrypted SSL (i.e., secure sockets layer) connection.

Figure 6:
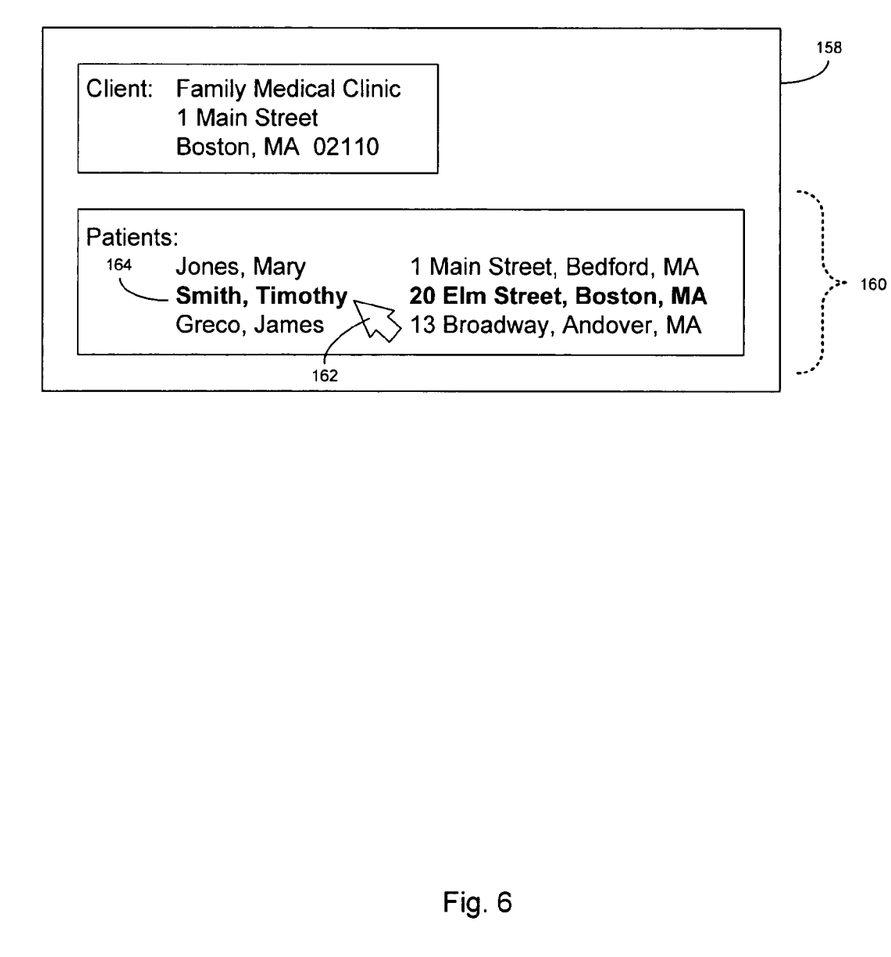
FIG. 6 is a diagrammatic view of a patient selection display screen rendered by the key organization system of FIG. 1.

Referring also to FIG. 6, when accessing key organization system 10, record processing module 62 provides the medical service provider 18 with a rendered screen display 158 that includes a list of patient identifiers 160. Patient identifiers 160 define the particular patient(s) who provided access keys to medical service provider 18 (i.e., granting medical service provider 18 access to various portions of their medical record (s)). The patient identifiers 160 may be any element that uniquely identifies the patient, such as the patient's name, the patient's social security number, or a unique patient number. In this particular example, Mary Jones is patient 20, Timothy Smith is patient 22 (as stated above), and James Greco is patient 24.

The presence of each of these names in the list of patient identifiers 160 indicates that a key was received from that patient. In order to access the medical record of a patient for which the medical service provider has an access key (i.e., for one of the patients listed in the list of patient identifiers 160), the medical service provider 18 selects the appropriate identifier using a mouse pointer 162 (or some other pointing device, not shown). For example, if the medical service provider wanted to access the medical record of Timothy Smith (i.e., patient 22), medical service provider 18 would typically double click (using a mouse) on the specific identifier 164 associated with Timothy Smith. Record processing module 62 would then, in turn, use access key 14 to access (i.e., retrieve, decrypt, and display) medical record 68, the medical record of Timothy Smith, i.e., patient 22.

Figure 7:
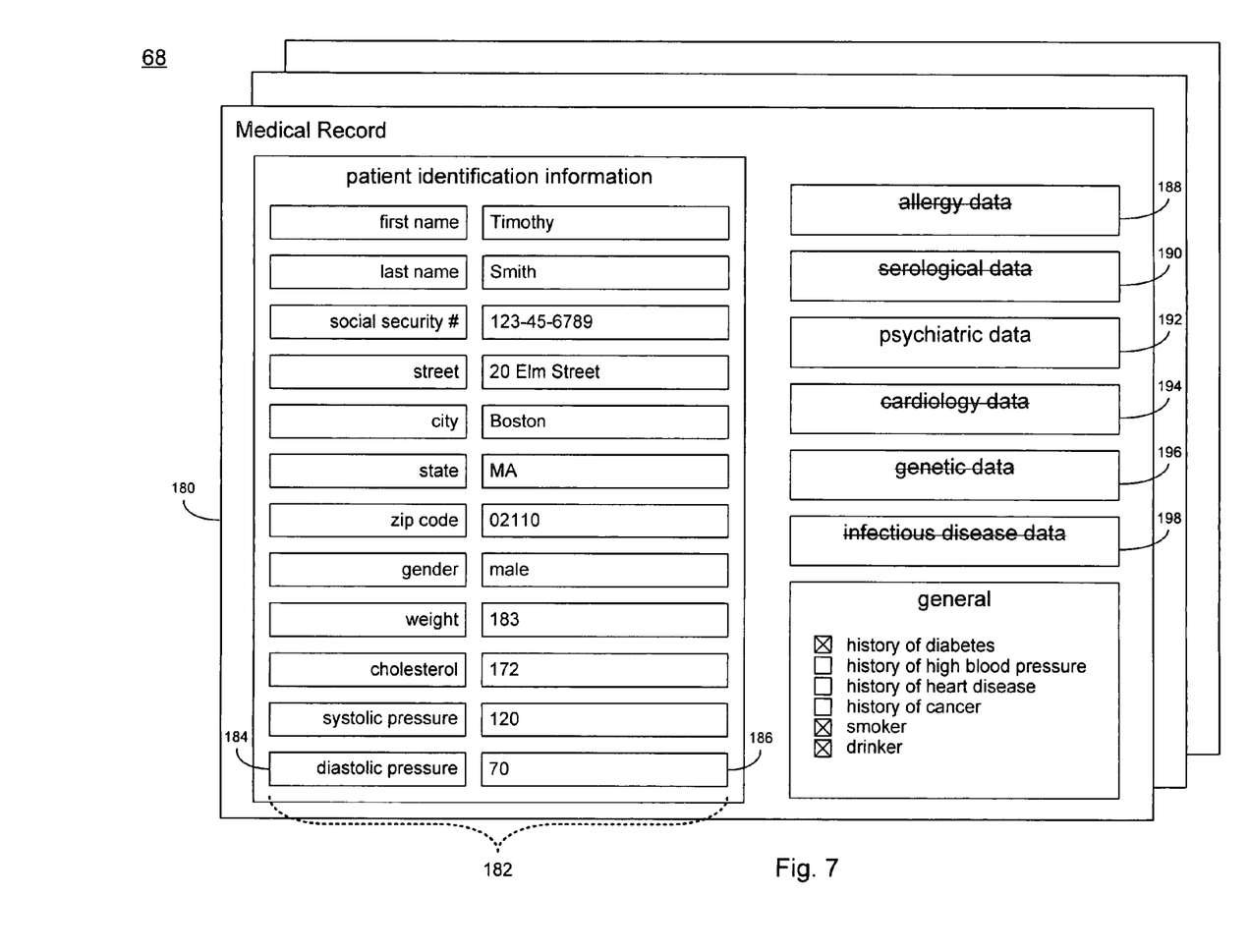
FIG. 7 is a diagrammatic view of a patient's medical record rendered by the key organization system of FIG. 1.

Referring also to FIG. 7, medical record 68 may be displayed in a separate window or displayed full screen on the display of client computer 34. As discussed above, the key provided to the medical service provider 18 only allows access to the portion(s) of the patient's medical record that the patient wishes to allow access. As discussed above, Timothy Smith (i.e., patient 22) is being treated by medical service provider 18 for depression and access key 14 grants access to the general and psychiatric portions of Timothy Smith's medical record.

However, access key 14 does not permit access (i.e., prohibits access) to the other portions of Timothy Smith's medical record, namely Allergies, Serological Data, Cardiology Data, Genetic Data, and Infectious Disease Data. Accordingly, these portions of the patient's medical record are unavailable.

Medical records (e.g., medical record 68) are typically database records 180 that define general patient data through the use of various data fields (e.g., data field 182), each of which includes a field name 184 and a field value 186. Field value 186 may define an amount (e.g., a patient's systolic pressure) or a binary condition (e.g., whether or not a patient is a smoker). Additionally, as discussed above, the medical records include Allergy data 188, serological data 190, psychiatric data 192, cardiology data 194, genetic data 196, and infectious disease data 198, each of which may be further broken down into data fields.

If the manner in which a patient utilizes a medical service provider changes, key maintenance module 58 allows a patient to modify or revoke the access key previously provided to the medical service provider.

Referring again to FIGS. 1, 2, 3 and 4, assume that patient 22 decides that he would like medical service provider 18 to monitor and treat him for a heart valve defect. Accordingly, patient 22 would want medical service provider 18 to have access to the cardiology data portion of their medical record. Therefore, patient 22 would use key maintenance module 58 to retrieve 106 the patient's copy of access key 14, which is being maintained 108 on patient key repository 54. Once retrieved, the patient can use display 120 to modify 110 the access key by adjusting the access parameters selected for that particular medical service provider. Continuing with the above-stated example, patient 22 would selected access parameter 128 (i.e., the parameter that grants access to the cardiology data portion) using mouse pointer 126.

This modified access key (i.e., access key 14') is then stored 102 on the patient key repository 54. Typically, the storing 102 of the amended version of the access key (i.e., access key 14') results in the deletion 112 of the older version of the access key (i.e., access key 14) from the patient key repository 54. However, if desired the patient may store the amended access key as a new access key (e.g., access key 72) without deleting the older version of the access key (i.e., access key 14).

As with a newly-generated access key, the amended version of the access key may be transmitted 104 to the appropriate medical service provider (e.g., medical service provider 108). As stated above, the medical service provider would then store amended access key 14' on their MSP key repository 54, thus allowing the medical service provider to access the patient's medical records with the revised level of access. However, when a determination 114 is made that an access key was amended (as opposed to being a new access key), it may be desirable to reconcile 116 the key repositories. This is due to the fact that if the medical service provider fails to store the amended access key on their MSP key repository, the medical service provider will continue to have the older level of access. This could prove problematic when the patient intends to reduce the level of access afforded to a medical service provider.

When reconciling 116 the patient key repository 54 and the MSP key repository 56, the access keys within the patient key repository are compared to the access keys with the MSP key repository. When this comparison is made, only the access keys (within the patient key repository) that were provided to the "intended-recipient" medical service provider are examined. Further, concerning the access keys within the MSP key repository, only access keys received from the "key-amending" patient are examined.

Continuing with the above-stated example, patient 22 (i.e., Timothy Smith) generated amended key 14' for medical service provider 18 (i.e., Family Medical Clinic). Therefore, all of the keys (within patient key repository 54) that patient 22 sent to medical service provider 18 are compared to all of the keys (within MSP key repository 56) that medical service provider 18 received from patient 22. Assuming that the original key 14 was deleted from patient key repository 54, the reconciliation process would compare amended key 14' (stored on patient key repository 54) to original key 14 (stored on MSP key repository 56). As amended access key 14' is newer than original access key 14, the reconciliation process would overwrite original access key 14 (stored in the MSP key repository) with amended access key 14' (stored in the patient key repository). As the medical service provider is typically not allowed to modify an access key, whenever different versions of the same access key are present on both the MSP key repository and the patient key repository, the MSP key repository is updated to include the version of the access key present on the patient key repository.

Figure 8:
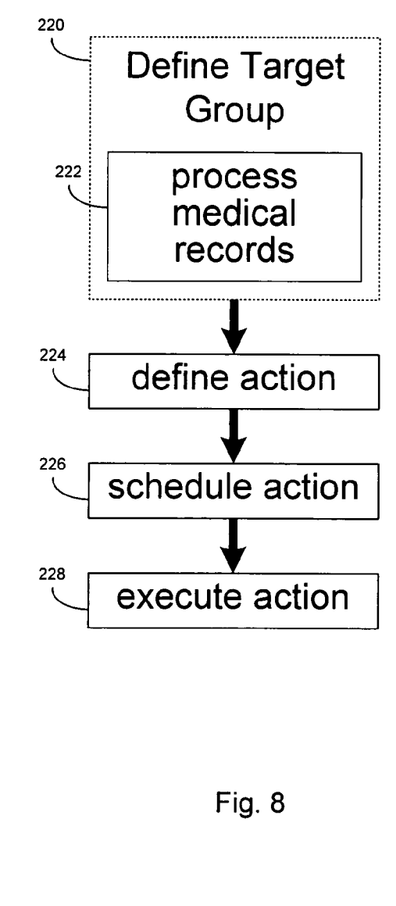
FIG. 8 is a block diagram of a rule processing module of the key organization system of FIG. 1.

Through the use of rule processing module 64, the medical service provider may define one or more rules for various groups of the patients to which they provide medical services. Rule processing module 64 allows medical service providers to defines rules that are applied to various groups of patients to which the medical service provider provides service.

Referring to FIGS. 1, 2, 7 and 8, processing module 64 allows the medical service provider 18 to define 220 a target group of patients that are chosen from existing group of patients of the medical service provider. As discussed above, these are the patients to which the medical service provider 18 has an access key that grants the medical service provider with access to at least a portion of the patient's medical records.

When defining a rule, the target group of patients may be defined in various ways. For example, the target group may be defined as all patients (i.e., of those being cared for by the medical service provider) that have a specific medical conditions (e.g., high blood pressure or diabetes). Additionally, the group may be defined as all patients that meet one or more physical criteria (e.g., all male patients, or all female patients over the age of fifty). Further, the group may be defined as all patients that have a certain habit (e.g., smoking or drinking) or perform an certain activity (e.g., joggers or skiers). Additionally, the membership within a group may be reduced by requiring the patients meet multiple criteria (e.g., male patients over the age of fifty that have a family history of prostate cancer). Alternatively, the membership within a group may be increased by requiring that the patients only meet one of several criteria (e.g., a male patient, or a patient over the age of fifty, or a patient with a family history of prostate cancer).

Typically the target group is defined by processing 222 the medical records of the existing patients that the medical service provider provides services to. When processing these medical records, rule processing module 64 examines the individual data fields (e.g., field 182) included within the medical record to determine which medical records include data fields having field values (e.g., field value 186) that match the various target criteria specified by the medical service provider.

In addition to defining the patients that are to be included in the target group, the medical service provider defines 224 the action to be taken with respect to the patients within the target group. Examples of the types of actions that may be defined include: posting a HTML link for a patient; posting a message for a patient; providing a tool to a patient (e.g., a diet monitoring software program); transmitting a email to a patient; updating a patient's medical record; transmitting a pop-up message to a patient; recommending that a patient join a discussion board; providing a patient with medical information; providing a medical report to a patient; providing a medical report to a third party; executing a program (e.g., executing the diet monitoring software program); and notifying a third party, for example. This list is not meant to be all inclusive and is only meant to provide examples of the types of actions that may be taken.

When defining a rule, the medical service provider also schedules 226 the execution time for the action. The action may be scheduled in various fashions. For example, the action may be scheduled to occur once (e.g., Dec. 1, 2003), multiple times (e.g., on Dec. 1, 2003 and Mar. 1, 2004), or may continuously repeat (e.g., the first of every month). Additionally, when defining a schedule, various scheduling criteria may be combined (e.g., once a day for a week, then once a week for a year, and then once a year indefinitely).

When defining a rule, the medical service provider typically uses a graphical user interface (not shown) that allows the medical service provider to define 220 the target group, define 224 the action, and schedule 226 the action.

Once the medical service provider defines a rule, rule processing module 64 executes 228 the action specified by the rule, which respect to the target group, on or after the execution time scheduled by the medical service provider.

Rule processing module 64 is typically a web-enabled application that is accessed by the medical service provider 18 through a browser application (e.g., Microsoft Internet Explorer™, or Netscape Navigator™) that is running on client computer 34.

When a patient logs into key organization system 10 through a browser application that is running on the patient's computer, the patient is typically presented with a graphical user interface (i.e., a desktop, not shown) that allows the patient to accomplish several tasks, such as create and/or modify access keys (e.g., through key maintenance module 58), review their own medical record(s), obtain web-based medical information, engage in web-based medical chat rooms, engage in web-based medical discussions groups, and join web-based medical forums, for example. Additionally, depending on whether the patient is included in a target patient group for an executed rule, the patient may be presented with, for example: an HTML link that is posted to their desktop; a message that is posted to their desktop message box, or a pop-up ad that appears on the patient's desktop, for example.

While key maintenance module 58 is described above as amending an access key to provide a medical service provider with an enhanced level of access, other configurations are possible. For example, the access key may be amended to provide a reduced level of access (with respect to the original access key). Further, the access key may be amended so that the amended access parameters do not provide access to any portion of the patient's medical records, effectively prohibiting the medical service provider from accessing the patient's medical records.

While centralized key repository 50, patient key repository 54, and MSP key repository 56 are described above as being located on a remote server, other configurations are possible. For example, the patient key repository may be stored locally on a computer operated by the patient. Further, the MSP key repository may be stored locally on a computer operated by the medical service provider. Additionally, as is known in the art, one or more of these repositories may be distributed across multiple computers/servers.

While rule processing module 64 is described above as creating "global" rules that apply to all of the patients of a medical service provider, other configurations are possible. For example, by defining the target group for a specific rule to be an individual patient, a "patient-specific" rule is created that applies only to that individual patient.

A number of implementations have been described. Nevertheless, it will be understood that various modifications may be made. Accordingly, other implementations are within the scope of the following claims.

What is claimed is:

1. A computer program product residing on a computer readable medium having a plurality of instructions stored thereon which, when executed by the processor, cause that processor to:
 receive user input from a medical service provider for defining a computer-executable rule for identifying one or more patients of said medical service provider who satisfy said rule;
 receive user input from said medical service provider for defining a computer-executable action to be taken concerning the identified one or more patients of said medical service provider who satisfy said rule;
 determine, for the computer-executable rule, an execution time for the action;
 process a plurality of computer-based medical records of patients for whom said medical service provider has an access key that grants the medical service provider access to said computer-based medical records against said computer-executable rule to identify one or more of said patients whose medical records satisfy the rule; and
 initiate, on or after the execution time, the action concerning the one or more patients whose medical records satisfy the rule.

2. The computer program product of claim 1 wherein the action includes one or more of:
 posting a HTML link for a patient;
 posting a message for a patient;
 providing a tool to a patient;
 transmitting an email to a patient;
 updating a patient's medical record;
 transmitting a pop-up message to a patient;
 recommending that a patient join a discussion board;
 providing a patient with medical information;
 providing a medical report to a patient;
 providing a medical report to a third party;
 executing a program; and
 notifying a third party.

3. The computer program product of claim 1 wherein the execution time is a single, non-recurring, execution time.

4. The computer program product of claim 1 wherein the execution time is a plurality of non-recurring execution times.

5. The computer program product of claim 1 wherein the execution time is a recurring execution time.

6. The computer program product of claim 1 wherein the instructions for processing the medical records against said rule comprises instructions for determining which of the medical records define the existence of a condition specified by said rule.

* * * * *